(12) United States Patent
Christensen (10) Patent No.: US 7,988,527 B2
(45) Date of Patent: Aug. 2, 2011

(54) BELLY AND BOTTOM ADJUSTABLE SUPPORT SYSTEM

(75) Inventor: Caroline West Christensen, Winsted, CT (US)

(73) Assignee: Caroline West Christensen, Winsted, CT (US)

( * ) Notice: Subject to any disclaimer, the term of this patent is extended or adjusted under 35 U.S.C. 154(b) by 573 days.

(21) Appl. No.: 12/102,062

(22) Filed: Apr. 14, 2008

(65) Prior Publication Data

US 2008/0254712 A1    Oct. 16, 2008

Related U.S. Application Data

(60) Provisional application No. 60/911,867, filed on Apr. 14, 2007.

(51) Int. Cl.
*A41C 1/08* (2006.01)
(52) U.S. Cl. .................................. 450/155; 128/99.1
(58) Field of Classification Search ............. 450/1, 155; 2/69, 69.5, 228, 238, 400, 406, 44, 45, 92, 2/455; 602/19; 128/99.1, 100.1, 101.1
See application file for complete search history.

(56) References Cited

U.S. PATENT DOCUMENTS

| | | | | |
|---|---|---|---|---|
| 4,789,372 A | * | 12/1988 | Wicks | 450/155 |
| 4,836,824 A | | 6/1989 | Seering et al. | |
| D365,397 S | | 12/1995 | Seering et al. | |
| D388,550 S | | 12/1997 | Seering et al. | |
| 5,702,286 A | * | 12/1997 | Seering et al. | 450/155 |
| 5,928,059 A | * | 7/1999 | Wicks | 450/155 |
| 6,159,070 A | * | 12/2000 | Schwartz et al. | 450/155 |

\* cited by examiner

*Primary Examiner* — Gloria Hale
(74) *Attorney, Agent, or Firm* — Cantor Colburn, LLP (57) ABSTRACT

A support system includes: an abdominal band for supporting weight of an abdomen of a user, the abdominal band adapted for encircling a lower portion of the abdomen and resting on hips and lower back of the user; a pair of shoulder straps, each shoulder strap adapted for passing over a respective shoulder of the user and fastening with the abdominal band over an anterior of the user and over a posterior of the user; and a pair of groin bands, each groin band adapted for passing under a crotch of the user and fastening with the abdominal band over an anterior of the user and over a posterior of the user. A method of use and another method for fabrication are provided.

12 Claims, 7 Drawing Sheets

BELLY AND BOTTOM ADJUSTABLE SUPPORT SYSTEM

CROSS REFERENCE TO RELATED APPLICATIONS

This application is filed under 37 CFR §1.53(b) and claims right of priority under 35 U.S.C. §119(e) to U.S. Provisional Patent Application No. 60/911,867, filed Apr. 14, 2007, which is incorporated by reference herein in its entirety.

BACKGROUND OF THE INVENTION

1. Field of the Invention

The invention disclosed herein relates to support for the abdomen, lower back, and groin, in particular, to a device and methods for using the device to provide needed support to men or women.

2. Description of the Related Art

As people age, they may be beset with a variety of medical conditions. One condition includes that of a distended abdomen. For example, both men and women may be overcome by obesity. Further, women may become pregnant. Often, the condition is severe enough that it presents physical challenges in the conduct of daily living.

Some attempts have been made to provide a short term remedy. For example, U.S. Pat. Nos. 4,836,824 and 5,702,286, both entitled "Prenatal Cradle" disclose a prenatal cradle or undergarment for use by obese individuals and pregnant women for supporting a baby, surrounding amniotic fluid, and associated matter in a pregnant woman's uterus by redistributing around the hips, torso and lower back downward and forward pressures exerted by the baby without inward movement towards the neck. The prenatal cradle is alleged to relieve strain on the woman's lower back, abdomen, and groin area. The prenatal cradle includes an adjustable womb band for supporting the uterus, and a pair of torso bands for redistributing the uterine weight across the torso. Connecting the womb band to the pair of torso bands is a pair of associated side members which distribute the uterine weight around the trunk of the woman, separating the torso bands and exposing the abdomen, supposedly to relieve groin pressure without imposing constricting inward pressure on the uterus. The patent also asserts that the prenatal cradle provides a method for ease of removal during Braxton Hicks contractions by loosening and positioning the front portion of the womb band above the uterus, returning the womb band below the uterus when the contractions have subsided.

Unfortunately, both versions of the prenatal have certain limitations. For example, the prenatal cradle includes components that are permanently affixed to each other. Accordingly, adjustment as well as replacement of components, such as those that wear, is not a simple process.

Therefore, what is needed is an improved abdominal support system.

BRIEF SUMMARY OF THE INVENTION

Disclosed is a support system that includes: an abdominal band for supporting weight of an abdomen of a user, the abdominal band adapted for encircling a lower portion of the abdomen and resting on hips and lower back of the user; a pair of shoulder straps, each shoulder strap adapted for passing over a respective shoulder of the user and fastening with the abdominal band over an anterior of the user and over a posterior of the user; and a pair of groin bands, each groin band adapted for passing under a crotch of the user and fastening with the abdominal band over an anterior of the user and over a posterior of the user.

Also disclosed is a method for supporting an abdomen of a user, that includes: donning an abdominal band by encircling a lower portion of the abdomen and fastening one end of the abdomen band to another portion thereof; resting the abdominal band on hips and lower back of the user; donning a pair of shoulder straps, by passing each shoulder strap over a respective shoulder of the user and fastening with the abdominal band over an anterior of the user and over a posterior of the user; and donning a pair of groin bands, by passing each groin band under a crotch of the user and fastening each groin support band with the abdominal band over an anterior of the user and over a posterior of the user.

Further disclosed is a method for fabricating a kit for a support system, the method including: selecting at least one material for fabrication of an abdominal band; a shoulder strap and a groin band; shaping the selected at least one material to provide a kit component, the component being one of the abdominal band; the shoulder strap and the groin band; equipping the kit component with at least one fastener; wherein each complete kit is configured with components for cooperatively providing the support system, where the system includes the abdominal band for supporting weight of an abdomen of a user, the abdominal band adapted for encircling a lower portion of the abdomen and resting on hips and lower back of the user; a pair of the shoulder straps, each shoulder strap adapted for passing over a respective shoulder of the user and fastening with the abdominal band over an anterior of the user and over a posterior of the user; and a pair of the groin support bands, each groin support band adapted for passing under a crotch of the user and fastening with the abdominal band over an anterior of the user and over a posterior of the user.

BRIEF DESCRIPTION OF THE DRAWINGS

The subject matter which is regarded as the invention is particularly pointed out and distinctly claimed in the claims at the conclusion of the specification. The foregoing as well as other features and advantages of the invention are apparent from the following detailed description taken in conjunction with the accompanying drawings in which:

DETAILED DESCRIPTION OF THE INVENTION

Disclosed herein is a "belly and bottom adjustable support system," or simply a "support system." The support system is both an abdominal and groin support system for individuals who have distended abdomens due to obesity, pregnancy, or other situations causing discomfort in the abdominal, back, and/or groin area. In general, the support system can be modified depending on the wearers comforts with the removable groin bands and shoulder bands.

Now with reference to FIGS. 1-7, there are shown aspects of the support system (100). In general, arrangement of the support system (100) may be modified depending on comfort of the wearer with removable groin bands (4, 5) and shoulder straps (2, 3). The support system (100) includes two removable shoulder straps (2, 3) which are fastened in the back (7, 9) and front portion (8,10) of the support onto the abdominal band (1). The shoulder straps are designed to either cross in the front at the chest (FIG. 2), in the back between the shoulder blades (FIGS. 1, 6), or run directly over each shoulder without crossing (FIG. 3), depending on comfort of the wearer and/or support required. The abdomen is supported by an abdominal band (1) which runs below the abdomen and up over the hips to the lower back. The abdominal band (1) fastens (6, 15) and opens on the side as it runs up toward the lower back to allow for removal and adjusting tightness. Two removable groin bands (4, 5) fasten to the abdominal band (1) in the front just above the groin (12, 14). The groin bands (4, 5) run between the wearers legs supporting the groin area and fasten in the rear (11, 13) at the back of the abdominal band (1).

In some embodiments, the support system (100) is made of a stretchable material such as sheet rubber, rubberized material, stretchable cloth and the like. Examples include materials marketed as "neoprene" and "spandex."

With reference to the drawings, the present invention includes five parts shown in the figures: the abdominal band (1), two shoulder straps (2, 3), and two groin bands (4, 5). Generally, the material used to fabricate the support system (100) is a stretchable material such as at least one elastomeric material, such as styrene butadiene rubber (SBR).

Exemplary materials may include, without limitation, and either singularly or in combinations, natural rubber; synthetic polyisoprene; butyl rubber (copolymer of isobutylene and isoprene); halogenated butyl rubbers (ChloroButyl Rubber; Bromo Butyl Rubber); polybutadiene; styrene-butadiene rubber (copolymer of polystyrene and polybutadiene); nitrile rubber (copolymer of polybutadiene and acrylonitrile); hydrogenated nitrile rubbers; chloroprene rubber; polychloroprene. Other materials may include saturated rubbers that cannot be cured by sulfur vulcanization, such as: EPM (ethylene propylene rubber, a copolymer of ethylene and propylene) and EPDM rubber (ethylene propylene diene rubber, a terpolymer of ethylene, propylene and a diene-component); epichlorohydrin rubber (ECO); polyacrylic rubber (ACM, ABR); silicone rubber (SI, Q, VMQ); fluorosilicone rubber (FVMQ); fluoroelastomers (FKM, and FEPM); perfluoroelastomers (FFKM); polyether Block Amides (PEBA); chlorosulfonated Polyethylene (CSM); and ethylene-vinyl acetate (EVA). In addition, various other types of elastomers may be used, such as: thermoplastic elastomers (TPE); thermoplastic vulcanizates (TPV); thermoplastic polyurethane (TPU); thermoplastic olefins (TPO); the proteins resilin and elastin as well as polysulfide rubber. Of course, materials may be used in the form of pure compounds, mixtures, weaves, layers and in other such embodiments.

One particular example of a material used for the abdominal band, shoulder and groin bands is that of 100% styrene butadiene rubber (SBR). Properties of the SBR neoprene include a tensile strength of about 5 kg/cm$^2$, minimum). The tear strength is about 2 (kg/cm$^2$, minimum). The hardness is about 6-8 degrees (type C), while the density is about 0.2+/−0.02 (g/cm$^2$), modulus at 200% elongation is about 4-5 (kg/cm$^2$), water absorption by weight percent is about 1 (maximum), shrinkage at 70 degrees Celsius over 24 hours is about 2 (maximum), and compression set is about 15 to 25, when compressed 50% at 25 degrees Celsius. Of course, other materials such as hook and loop fasteners (such as VELCRO™ type fasteners) may be adorned onto the materials, fabricated into the materials and the like.

In addition, the abdominal band (1), the shoulder straps (2, 3), and the groin bands (4, 5) may be lined with other fabrics such as, but not limited to: nylon mesh weave, cotton, foam, and/or fleece. The additional layers may be needed for added support, moisture absorption, a holding layer (such as for an ice pack), and/or comfort padding.

A variety of fastening systems may be used. For example, aside from hook and loop type fasteners, clasps, buttons, snaps, zippers, other suitable fasteners and any combination of the foregoing may be used.

Further, the abdominal band (1), the shoulder straps (2, 3), and the groin bands (4, 5) may be adorned with pockets and similar devices. For example, the pockets may provide for holding of the ice pack or for convenient storage or personal items, such as a money clip or cell phone. Any one of the abdominal band (1), the shoulder straps (2, 3), and the groin bands (4, 5) may have ornamentation, such as a colored fabric laminated to the exterior thereof, or any other such adornment.

Generally, the abdominal band (1) has loop fabric, which is hook fastener compatible, laminated to the exterior thereof.

In one embodiment, of the hook fastener as the fastening device, the hook fastener is attached with #B-69 bonded nylon sewing thread with a zig-zag and/or a straight stitch. The thread type may vary depending on, for example, availability and development of higher quality materials, cost and other such factors. In some embodiments, the hook fastener is industrial strength and ranges in size from about 0.5 inches to about 23 inches in width. In other embodiments, the fastener(s) may be coupled by being sewed, glued, bonded, laminated onto, fabricated into, or by any other similar technique.

Figure 7:
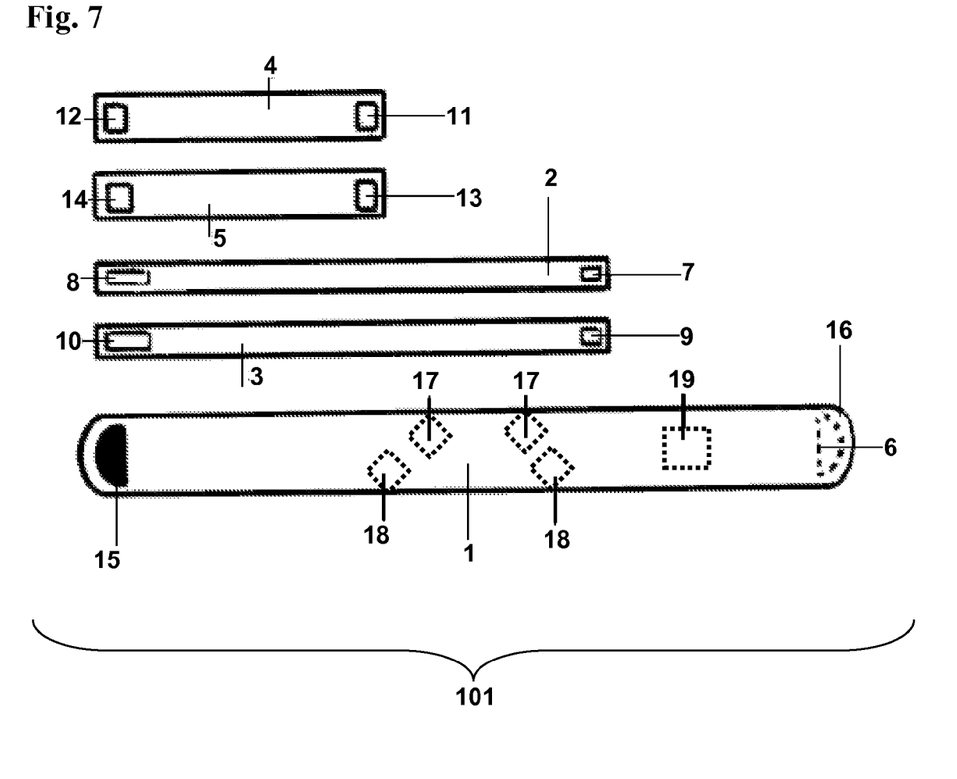
FIG. 7 depicts a kit including components of the support system in an unassembled state.

The abdominal band (1) varies in length depending on the size of the individual. For example, sizes may range from about two feet in length to about nine feet. Generally, the width of the abdominal band is between about two inches to about twenty four inches, also depending on the size of the wearer. Each end of the abdominal band (1) may be rounded (16), as shown in FIG. 7. On the outer end of the abdominal band (1), a hook fastener may be attached (15), generally following an outline of the fabric, while leaving a margin of fabric (such as between about one eighth of an inch to about one half of an inch). The hook fastener may be half-moon-shaped and sewn to the fabric. On the inner portion of the right side of the abdominal band, a half-moon-shaped piece of hook fastener (6) may be sewn following the outline of the fabric, leaving about one eighth of an inch to about one half of an inch margin of fabric outlined. On the inner portion of the right side of the abdominal band a square piece of hook fastener may be sewn (19) to hold the two sides of the fabric together.

The two shoulder straps (2, 3) (also referred to as "bands") vary in length and width depending on the size of the individual wearing the support system (100). The shoulder straps (2, 3) may vary in dimensions from about twelve inches to about eighty inches long and from about one inch to about five inches wide. Generally, the shoulder straps are equal in width for the entire length of the strap. In some embodiments, both ends of the shoulder straps are terminate with squared off ends. As shown in FIG. 7, hook fastener material, which follows the outline of each end (7, 8, 9, 10) in the illustrations, may be sewn to the inside of the stretchable fabric. In some embodiments, the hook fastener sewn to the front of the shoulder straps (8,10) is double the length of that which is sewn to the back of the shoulder straps (7,9).

The two groin bands (4, 5) vary in length and width depending on the size of the individual. The length is between seven inches and seventy inches long, and the width may be between about half an inch and about eight inches wide. The groin bands (4, 5) may be equal in width for the entire length of the band, but this is not required. Both ends of each selected groin band may terminate with squared ends. Generally, attached to the inside of the end of each groin band is a fastener, such as a hook fastener. Shown in FIG. 7 and other figures, the hook fasteners (11, 12, 13, 14) are sewn onto the fabric and follow the outline of each end of the material. The following instructions describe a method for a user to don the support system (100).

First, the user (also referred to as a "wearer") places the middle of the abdominal support band at the center of the lower back. The wearer wraps the left side of the abdominal band over the left hip and under the protruding abdomen. Secondly, the wearer wraps the right side of the abdominal band over the right hip and under the protruding abdomen fastening the outer abdomen band fastener (6) to the outer fabric of the left side of the band. The inner abdomen band fastener (15) fastens to the inside of the right side of the abdominal band. The abdominal band may be worn alone if the wearer is not in need of the extra support provided by the shoulder straps (2, 3) and groin bands (4, 5).

Figure 1:
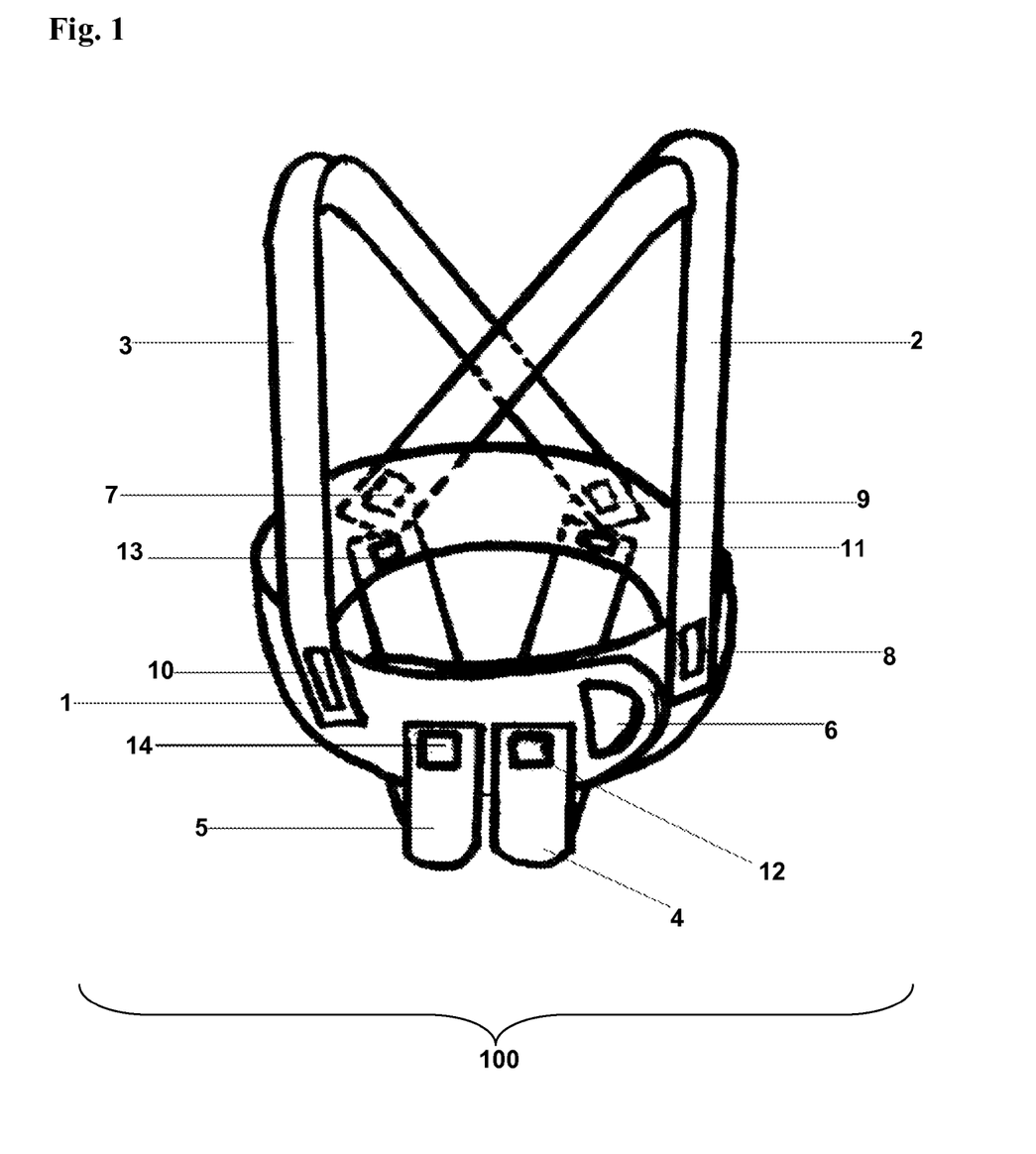
FIG. 1 is a front view of a belly and bottom adjustable support system
Figure 2:
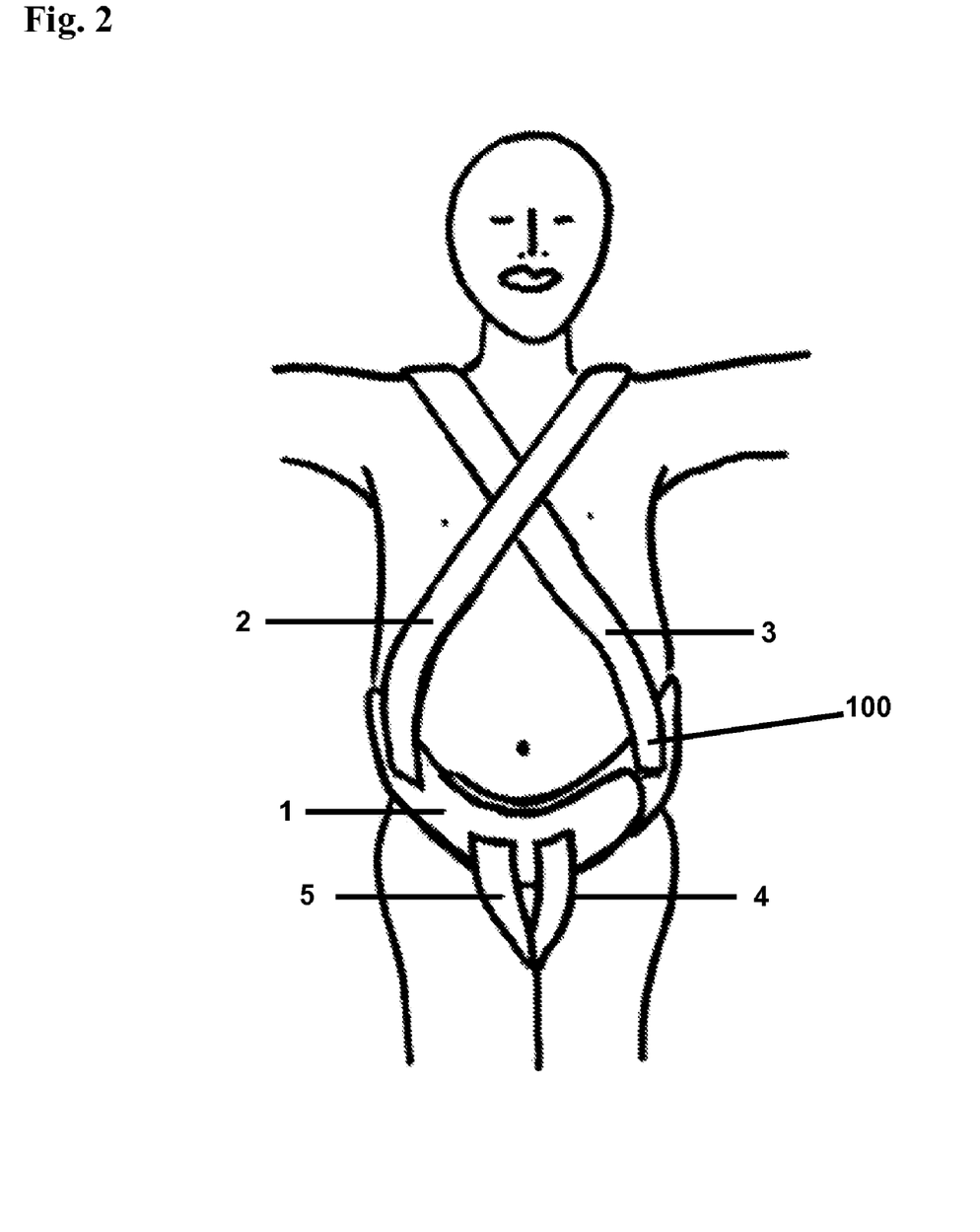
FIG. 2 is a front view of a user wearing the support system.
Figure 3:
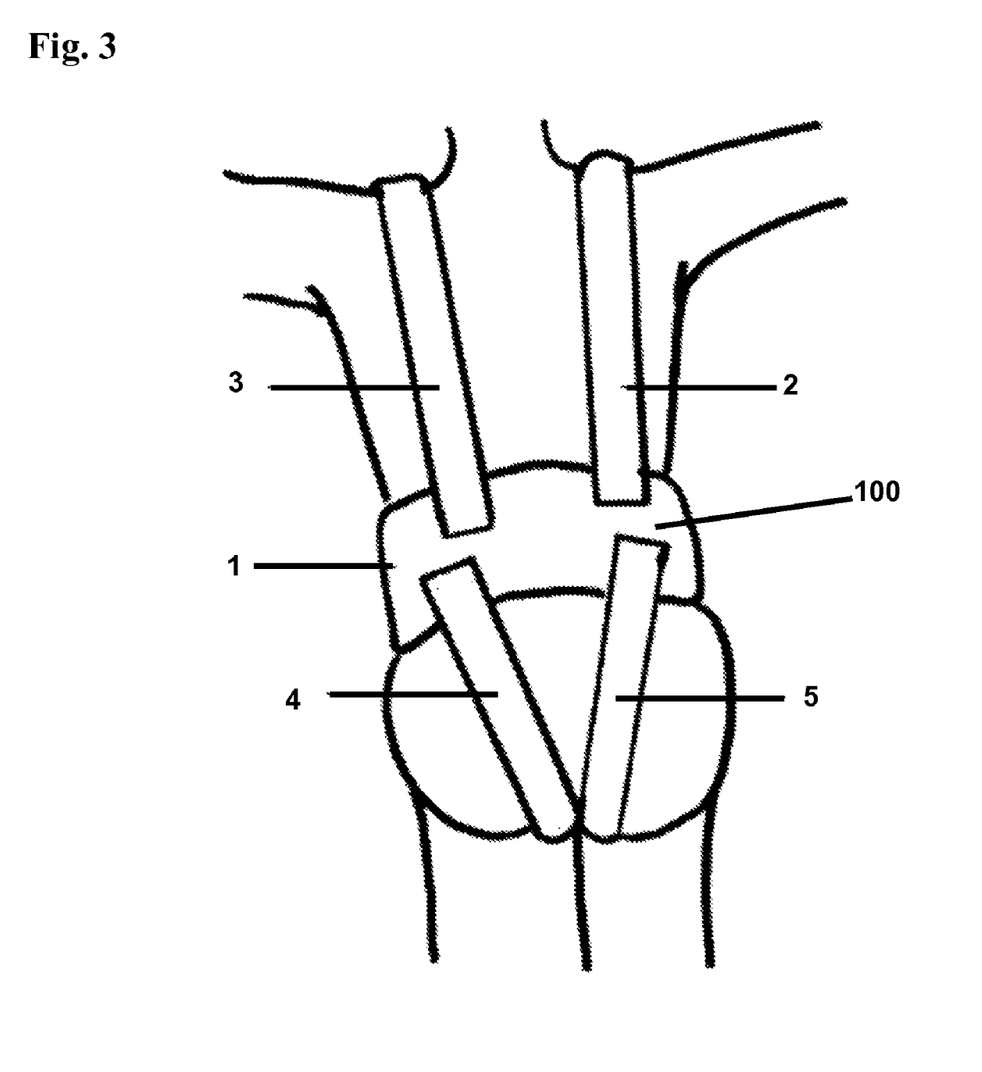
FIG. 3 is a rear view of the user wearing the support system.
Figure 4:
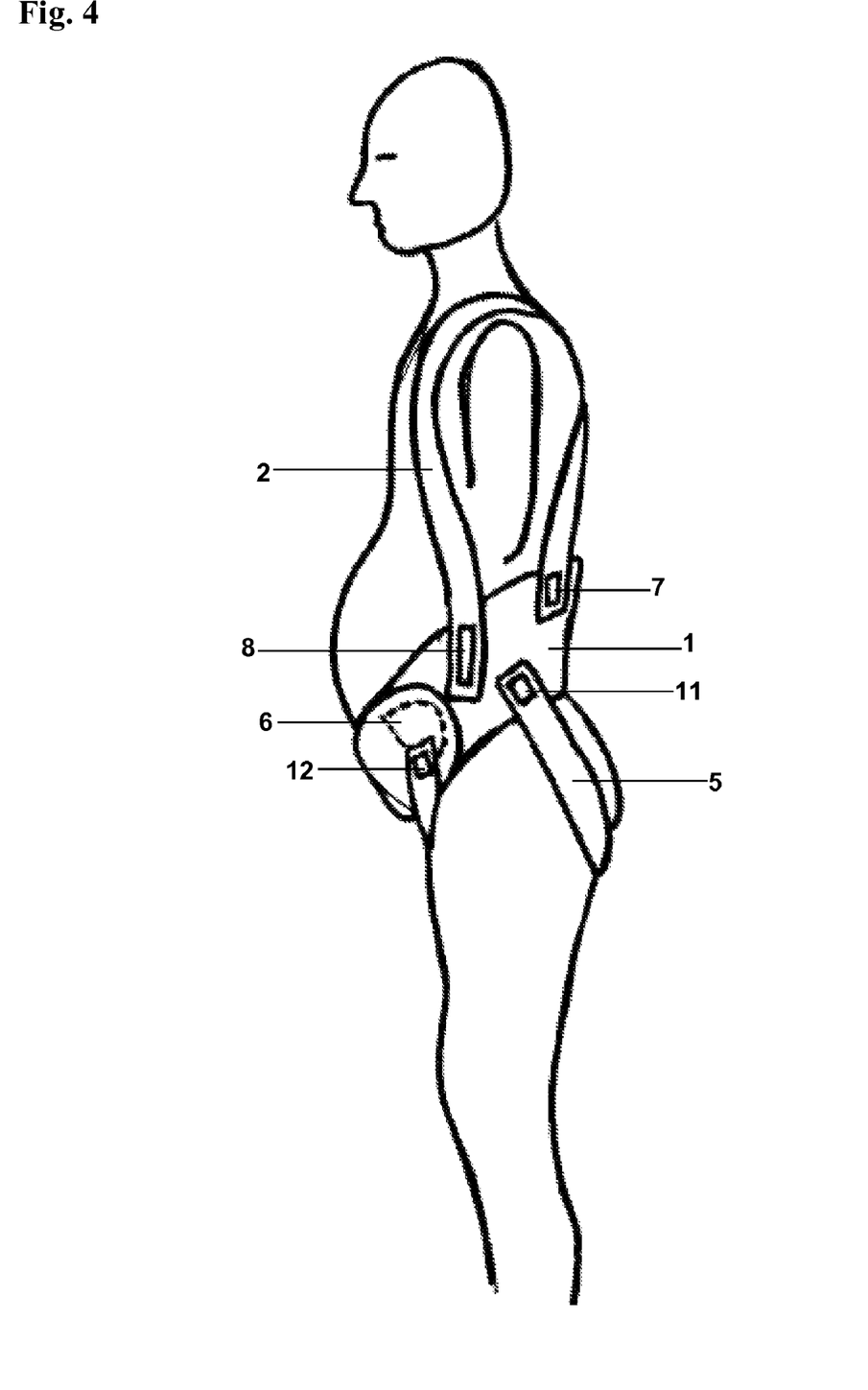
FIG. 4 is a side view of the user wearing the support system.
Figure 5:
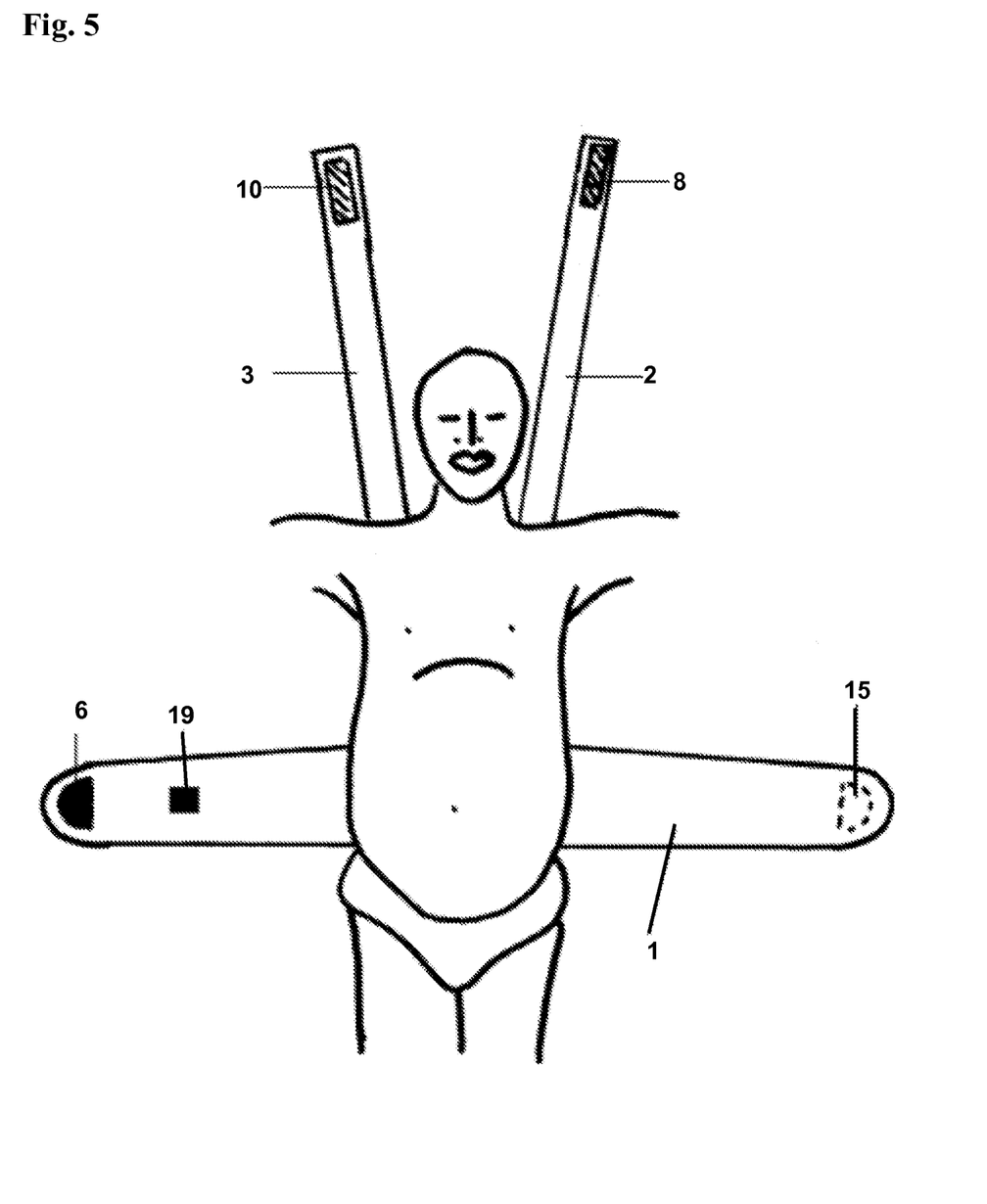
FIG. 5 is a front view of the user wearing the support system with the system unfastened.
Figure 6:
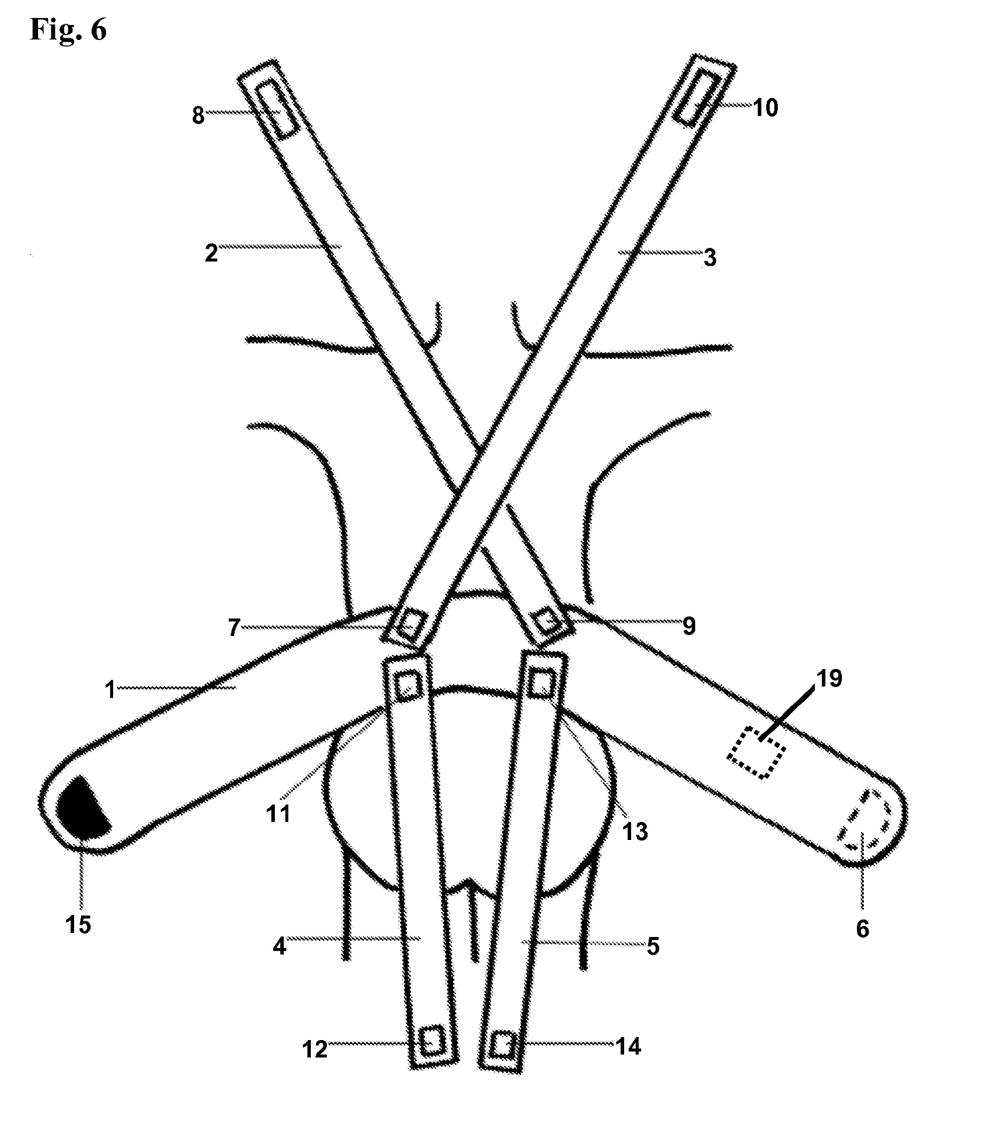
FIG. 6 is a rear view of the user wearing the support system with the system unfastened.

The shoulder straps (2, 3) may be added as increased support is needed (i.e. with increased weight of a growing fetus, or increase of abdominal weight due to obesity). The wearer fastens the right rear and left rear fasteners of the shoulder straps (7, 9) to the right and left suggested guide marks (17) on the abdominal band (1), shown in FIG. 7. Depending on comfort of the wearer, the shoulder straps (2, 3) may be brought directly over each shoulder (FIG. 3), crossed at the upper back and brought over each shoulder (FIGS. 1, 6), brought straight from the back over each shoulder and crossed in the front at the chest (FIG. 2), or crossed in the back (posterior) and in the front (anterior). For all four options, the shoulder straps (2, 3) may be fastened in the front onto the abdominal band (1) on the side of the abdomen (FIGS. 2, 4). The tightness of the shoulder strap may be adjusted by the wearer by fastening the fastener higher or lower on the abdominal band (1).

The groin bands (4, 5) may be added to support system (100) if the wearer is in need of groin support due to various discomforts (e.g., vulvar varicose veins due to increasing weight of pregnancy, inguinal hernia, prolapsed genitals, uterus, or bladder, swelling of the pubic region). The groin bands (4, 5) may be fastened with the right and left rear fasteners (11, 13) at the suggested guide marks (18) on the back of the abdominal band. The groin bands (4, 5) may then be brought through the legs, and generally placed snugly under a crotch of the wearer. The groin bands (4, 5) may be crossed or kept parallel depending on comfort of the wearer. The groin bands (4, 5) may be fastened in the front onto the abdominal band (1) with the right and left front fasteners (12, 14). The positioning of the front of the groin band (4, 5) may vary depending on the support need by the wearer. The tightness of the groin bands (4, 5) may vary depending on the comfort of the wearer and can be lowered or raised on the front or rear of the abdominal band (1).

In various embodiments, the wearer need not make use of guide marks (17, 18). That is, in various embodiments, the abdominal band (1) includes a loop type of fastener over the entire outer surface, such that the wearer is able to fasten ends of the shoulder straps (2, 3) or groin bands (4, 5) (each end having a hook style fastener) anywhere on the outer surface of the abdominal band (1). In further embodiments, the abdominal band (1) includes the a loop type of fastener over the entire inner surface, both the inner surface and the outer surface, or in portions thereof, and in other such arrangements.

As shown in FIG. 2, each of the shoulder straps (2,3) and the groin bands (4,5) may be coupled to the abdominal band (1) on the anterior of the user. The coupling on the anterior may be on an outside portion of the abdominal band (1), as shown, or on an inside portion of the abdominal band (1). Also, as shown in FIG. 3, each of the shoulder straps (2,3) and the groin bands (4,5) may be coupled to the abdominal band (1) on the posterior of the user. The coupling on the posterior may be on an outside portion of the abdominal band (1), as shown, or on an inside portion of the abdominal band (1). Of course, it should be recognized that the terms "anterior" and "posterior" are relative terms, and that optimal placement of the couplings may be determined according to comfort of the user, ability to support, and by other such factors. Reference may be had to FIG. 4, which depicts the anterior mounting of the shoulder strap 2 actually oriented along a left side of the user and coupled to the abdominal band (1) there.

In some embodiments, at least one of the shoulder straps (2, 3) and the groin bands (4, 5) may include a buckle (not shown), as is known in the art, for adjusting a length thereof. Such buckles are commonly used for adjusting the lengths of straps on luggage, laptop cases, camera cases, and the like. Each buckle generally provides for adjusting a length by doubling up material in the respective strap or band.

Figure 8:
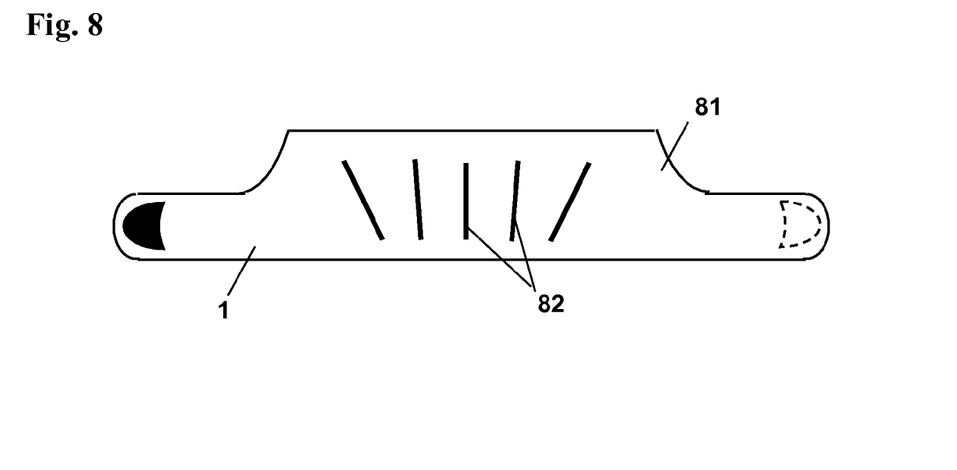
FIG. 8 depicts another embodiment of an abdominal belt.

FIG. 7 displays exemplary patterns used to make a kit (101) of components. The components are assembled to provide the support system (100). When fabricating components of the kit (101), a manufacturer may simply cut, stamp, mold, print or otherwise shape a selected material, or combination of materials to produce each component. It should be noted that the dimensions and particular shapes of each of the components as disclosed herein is merely illustrative and non-limiting. For example, the abdominal band (1) may include a support portion for extending upward along a back of the wearer. Reference may be had to FIG. 8.

In FIG. 8, the abdominal band (1) includes an additional support feature (81). In some embodiments, the abdominal band (1) includes at least one receptacle for receiving at least one stiffener (82). The stiffener (82) may be formed of metal, hard or soft plastic, wood or of any other material or combination of materials suited for use as a stiffener 82. Generally, a plurality of stiffeners (82) may be inserted into pockets or layers or other such receptacles within the abdominal band (1). Stiffeners may be replaced, removed or supplemented as needed.

It should be noted that the terms "band" and "strap" as used herein are generally interchangeable.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation, material, dimension or method of the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A support system for obese, hernia patients and/or pregnant wearers comprising:
 a kit, including;
 an abdominal band for supporting weight of an abdomen of a user, the abdominal band having a body, first and second fasteners at opposing ends thereof and first interior and second exterior pairs of guide marks disposed between the opposing ends, and the abdominal band being adapted for encircling a lower portion of the abdomen and resting on hips and lower back of the user;
 a first shoulder strap having a front and a rear fastener at opposing ends thereof;
 a second shoulder strap having a front and a rear fastener at opposing ends thereof, each of the first and second shoulder straps being separately adapted for passing over a respective shoulder of the user and fastening with the abdominal band at the body and the first interior guide marks over an anterior of the user and over a posterior of the user;
 a first groin band having a front and a rear fastener at opposing ends thereof; and
 a second groin band having a front and a rear fastener at opposing ends thereof, each of the first and second groin bands being separately adapted for passing under a crotch of the user and fastening with the abdominal band at the body and the second exterior guide marks over an anterior of the user and over a posterior of the user.

2. The support system of claim 1, wherein at least one of the fasteners comprises a hook and loop.

3. The support system of claim 1, wherein at least one of the fasteners comprises at least one of a clasp, a button, a snap and a zipper.

4. The support system of claim 1, wherein one of the abdominal band, the shoulder straps and the groin bands is fabricated from styrene butadiene rubber.

5. The support system of claim 1, wherein the first and second fasteners of the abdominal band comprises a loop style fastener over at least one of an outer surface and an inner surface.

6. The support system of claim 1, wherein the abdominal band comprises a receptacle for receiving at least one stiffener.

7. The support system of claim 1, wherein at least one of the abdominal band, the shoulder straps and the groin bands comprises ornamentation.

8. The support system of claim 1, wherein at least one of the abdominal band, the shoulder straps and the groin bands comprises a pocket.

9. The support system of claim 1, wherein one of the abdominal band, the shoulder straps and the groin bands comprises a lining of at least one of nylon mesh weave, cotton, foam, and fleece.

10. A method for fabricating a kit for a support system for obese, hernia patients and/or pregnant wearers, the method comprising:
 selecting at least one material for fabrication of an abdominal band; first and second shoulder straps and first and second groin bands;
 shaping the selected at least one material to provide a kit component, the component being one of the abdominal band; the first and second shoulder straps and the first and second groin bands;
 equipping the kit component with at least one fastener;
 wherein each complete kit is configured with components for cooperatively providing the support system, and includes:
 the abdominal band having a body, first and second fasteners at opposing ends thereof and first interior and second exterior pairs of guide marks disposed between the opposing ends, the abdominal band being adapted for encircling a lower portion of the abdomen and resting on hips and lower back of the user;
 the first shoulder strap having a front and a rear fastener at opposing ends thereof;
 the second shoulder strap having a front and a rear fastener at opposing ends thereof, each of the first and second shoulder straps being separately adapted for passing over a respective shoulder of the user and fastening with the abdominal band at the body and the first interior guide marks over an anterior of the user and over a posterior of the user;
 the first groin band having a front and a rear fastener at opposing ends thereof; and
 the second groin band having a front and a rear fastener at opposing ends thereof, each of the first and second groin bands being separately adapted for passing under a crotch of the user and fastening with the abdominal band at the body and the second exterior guide marks over an anterior of the user and over a posterior of the user.

11. The method as in claim 10, wherein shaping comprises at least one of cutting, stamping and molding the selected at least one material.

12. The method as in claim 10, wherein the at least one material comprises an elastomeric material.

* * * * *